United States Patent [19]

Fernandes et al.

[11] 4,440,679

[45] Apr. 3, 1984

[54] PASTEURIZED THERAPEUTICALLY ACTIVE PROTEIN COMPOSITIONS

[75] Inventors: Peter M. Fernandes, Concord; John L. Lundblad, El Cerrito, both of Calif.

[73] Assignee: Cutter Laboratories, Inc., Berkeley, Calif.

[21] Appl. No.: 451,645

[22] Filed: Dec. 20, 1982

Related U.S. Application Data

[63] Continuation of Ser. No. 127,351, Mar. 5, 1980, abandoned.

[51] Int. Cl.³ .................. A61K 35/16; A61K 37/02; A61K 37/06; C07G 7/00
[52] U.S. Cl. .................. 260/122; 260/112 R; 260/112 B; 424/85; 424/101; 435/188
[58] Field of Search ............... 260/112 B, 122, 112 R; 424/101, 85; 435/188

[56] References Cited

U.S. PATENT DOCUMENTS

| | | | |
|---|---|---|---|
| 2,495,298 | 1/1950 | Szent-Gyorgyi et al. | 260/112 B |
| 2,705,230 | 3/1955 | Reid | 260/122 |
| 2,765,299 | 10/1956 | Porsche et al. | 260/122 |
| 2,897,123 | 7/1959 | Singher | 424/101 X |
| 3,041,242 | 6/1962 | Barr et al. | 260/112 B X |
| 3,057,781 | 10/1962 | Mace et al. | 260/112 B X |
| 3,227,626 | 1/1966 | Baumgarten et al. | 424/94 X |
| 3,926,939 | 12/1975 | Ivanov et al. | 260/122 |
| 3,992,367 | 11/1976 | Plan et al. | 260/122 |
| 4,046,877 | 9/1977 | White et al. | 424/177 |
| 4,061,735 | 12/1977 | Funakoshi et al. | 424/177 |
| 4,075,197 | 2/1978 | Schuck et al. | 260/122 |
| 4,137,307 | 1/1979 | Funakoshi et al. | 424/177 |
| 4,168,300 | 9/1979 | Andersson et al. | 260/112 B X |
| 4,177,188 | 12/1979 | Hansen | 424/101 X |
| 4,178,368 | 12/1979 | Heimburger et al. | 424/94 |
| 4,279,344 | 10/1981 | Schwinn | 260/112 B |
| 4,341,764 | 7/1982 | Wallace et al. | 424/101 |

OTHER PUBLICATIONS

Arch-of Biochem., vol. 3 (1944), Seegers, pp. 363–367.
J. of Clin. Investigation, vol. 27 (1948), pp. 239–244, Gellis et al.
Biochemistry, vol. 18, No. 23, pp. 5191–5196 (Nov. 1979), Back et al.

*Primary Examiner*—Howard E. Schain
*Attorney, Agent, or Firm*—Theodore J. Leitereg; Lester E. Johnson

[57] ABSTRACT

Compositions containing thermally sensitive, therapeutically active proteins are pasteurized without substantial loss of therapeutic activity by mixing the protein composition with a pasteurization-stabilizing amount of a polyol prior to pasteurization. Pasteurized compositions containing therapeutically active proteins, which have heretofore been unattainable, can be prepared by the method of the invention.

25 Claims, 1 Drawing Figure

FIG. 1

PASTEURIZED THERAPEUTICALLY ACTIVE PROTEIN COMPOSITIONS

This application is a continuation of application Ser. No. 127,351, filed Mar. 5, 1980, now abandoned.

BACKGROUND OF THE INVENTION

1. Field of the Invention

This invention relates to and has among its objects novel compositions for therapeutic use and methods of making them. It is a particular object of this invention to provide pasteurized compositions containing therapeutically active proteins. Further objects of the invention will be evident from the following description.

2. Description of the Prior Art

Many useful blood fractions and blood proteins are obtained from human blood plasma by fractionation according to known techniques such as, for example, the alcohol fractionation method of Cohn described in U.S. Pat. No. 2,390,074 (1945) and the *Journal of the American Chemical Society*, Vol. 68, page 459 (1946) and the Rivanol ®-ammonium sulfate method. The aforementioned methods as well as other variations and techniques are summarized in "The Plasma Proteins", second edition, Volume III, pages 548–550, Academic Press, New York, N.Y. (1977). These blood fractions contain biologically active proteins that possess certain therapeutic qualities. For instance, Factor VIII or antihemophilic factor is useful against hemophilia; plasminogen is a precursor of plasmin for treatment of acute thromboembolic disorders; immune serum globulin (IgG) is employed in the treatment of congenital gamma globulin deficiency, measles, poliomyelitis and hepatitis A and B; fibronectin has been identified as active in treatment of burns, shock, cancer, etc.; antithrombin III is a coagulation inhibitor, cryoprecipitate itself may be used directly for classic hemophilia; Plasma Protein Fraction (human) and albumin are useful in treatment of shock due to burns, crushing injuries, abdominal emergencies, and any other cause producing a predominant loss of plasma fluids and not red cells; immune globulin, intravenous (modified immune serum globulin) is a substitute for immune serum globulin administerable in larger quantities; Factor VIII inhibitor bypassing active (FEIBA) substance described in U.S. Pat. No. 4,160,025 as a blood-coagulation-promoting preparation for Factor VIII inhibitor patients; $\alpha$-1-antitrypsin can be employed in the treatment of emphysema; plasma growth hormone corrects pituitary growth deficiency, somatomedin is useful in correcting growth deficiencies, other immune serum globulins, e.g., IgA, IgD, IgE, and IgM, may be employed to treat various immune protein deficiencies; prealbumin (U.S. Pat. No. 4,046,877) is employed to increase immunologic competence; plasminogen-streptokinase complex (U.S. Pat. No. 4,178,368) can be administered to patients for treatment of thromboembolisms; ceruloplasmin, transferrin, haptoglobin, and prekallikrein have reagent and other uses.

One problem confronting users of plasma, plasma fractions, and compositions containing individual blood proteins is the thermal instability of the therapeutically active proteins contained therein. In many cases, substantial, and sometimes complete, losses of activity are observed if these proteins are heated above physiological temperatures, i.e., above about 40°–45° C. Consequently, these items require special care during preparation and storage to minimize such deactivation.

The thermal instability of the aforementioned proteins renders them unpasteurizable. Therapeutically active proteins isolated from plasma may contain viruses, e.g., hepatitis virus, present in the source material for the protein fraction, namely, blood from a donor. A risk of contracting hepatitis exists, therefore, for those receiving unpasteurized fractions from blood plasma fractionation because the presence of the virus cannot be detected with certainty by any known procedure. In a large number of situations, this risk is outweighed by the detriment to a patient in not receiving the therapeutic plasma fraction as determined by the physician.

Some therapeutically active proteins derived from plasma have been pasteurized successfully. For example, it is well known that albumin can be pasteurized by heating at 60° C. or 64° C. for 10 hours (Gellis et al., *J. Clin. Invest.*, Vol. 27, pages 239–244 (1948)) in the presence of certain stabilizers such as acetyl-tryptophan and sodium caprylate. Individuals receiving this pasteurized material did not contract hepatitis, thus indicating the inactivation of hepatitis virus while retaining the activity of albumin under the afore-described heating conditions. Plasma Protein Fraction (human) is also stabilized during pasteurization by the above method.

A process for pasteurizing plasminogen is disclosed by Baumgarten et al. in U.S. Pat. No. 3,227,626. An aqueous preparation containing 0.25–20 milligrams per milliliter (mg/ml) of plasminogen and further containing 0.1–0.5 molar lysine with a pH of 5.3–7.5 was heated at 60° C. for 10 hours. As the patentee states, hapatitis virus was destroyed and the danger of transmitting hepatitis was removed with retention of plasminogen activity. Attempts to pasteurize plasminogen under the above conditions in the absence of lysine resulted in complete destruction of plasminogen activity. It is interesting to note that plasminogen cannot be stabilized with N-acetyl-tryptophan and sodium caprylate during pasteurization, nor can albumin and Plasma Protein Fraction (human) be pasteurized in the presence of lysine.

Singher has described a process for treating plasminogen to produce a material that is not contaminated with hepatitis virus (U.S. Pat. No. 2,897,123). In the patented pasteurization technique aqueous solutions of plasminogen are heated at about 60° C. for about 10 hours. The activity of plasminogen is retained if the solutions have a pH in the range not less than 3 nor greater than 6.5 and an ionic strength not greater than 0.3.

Another method for removing hepatitis virus from a biological material is described in U.S. Pat. No. 4,168,300. The material to be treated is contacted with a preparation, which may be agarose gel or beaded polyacrylamide plastic coupled with a variety of hydrophobic ligands. Plasma and albumin were subjected to the above purification technique to remove hepatitis virus.

Aqueous solutions of the enzyme thrombin have been stabilized (Seegers, *Arch. Biochem.*, 1944, Vol. 3, pages 363–367) during heating at 50° C. in the presence of saturation amounts of certain glycosides. The stabilized solutions were heated at the above temperature for a period of 48 hours or more with minimal loss of activity. On the other hand, Seegers also discloses that glycosides and polyols have only minimal effectiveness in stabilizing the enzyme prothrombin. The reversible denaturation of lysozyme and ribonuclease was studied by Gerlsma et al., *Int. J. Peptide Protein Res.*, Vol. 4, pages 377–383 (1972). The authors found that certain polyhydric alcohols increased somewhat the temperatures at which these enzymes were denatured. Finally, Simpson et al., in *J. Am. Chem. Soc.*, Vol. 75, No. 21, pages 5139–5152 (1953) and Donovan in *J. Sci. Fd. Agric.*, Vol. 28, pages 571–578 (1977) noted that the denaturation temperature of ovalbumin (an egg white protein) was raised slightly in the presence of sucrose in aqueous solutions of the protein. However, Donovan points out that the temperatures of denaturation of ovalbumin and S-ovalbumin are 84.5° C. and 92.5° C., respectively. Furthermore, ovalbumin and S-ovalbumin, as well as the aforementioned enzymes, have no therapeutic activity in treating disorders in humans, whereas blood plasma proteins are therapeutically active. In fact, as mentioned below, proteolytic enzymes deactivate blood plasma proteins.

Singher, in the aforementioned U.S. Patent, lists some methods of destroying hepatitis virus. The least effective of these methods involves the use of either nitrogen mustard or β-propiolactone. High energy irradiation in appropriate dosage is effective but destroys biological activity when applied to human blood products. Heat is recognized also as effective against hepatitis virus, the preferred treatment being heating the material at 60° C. for 10 hours. Higher temperatures above 70° C. for shorter intervals or lower temperatures for longer intervals have also been tried with successful results. However, it is important to note that higher temperatures are undesirable because of the potential for denaturation of the proteins. Furthermore, lower temperatures for long intervals are to be avoided because various proteolytic enzymes are activated under these conditions, and these activated enzymes cause protein degradation. Also, the use of temperatures lower than 60° C. for pasteurization has not been shown to consistently yield a material that does not contain the infective virus.

As mentioned above, the recognition that heating at 60° C. and 64° C. for 10 hours successfully destroys the hepatitis virus in albumin was made by Gellis et al., supra. Gellis et al. proved experimentally that albumin heated under the above conditions did not transmit hepatitis even if hepatitis virus was present prior to pasteurization. However, the author noted that hepatitis virus survived heating at 56° C. for one hour, a temperature usually employed for the inactivation of viruses. Thus, although heating at temperatures of about 56° C. for one hour will deactivate most viruses, hepatitis virus is not inactivated; and materials containing hepatitis virus, which are heated at 56° C. for one hour, cause infection of hepatitis in individuals receiving such materials.

SUMMARY OF THE INVENTION

The invention described herein provides means for obviating the above-outlined problems. In the method of the invention certain compositions containing thermally sensitive, therapeutically active proteins are rendered heat stable during pasteurization or heating at a temperature of about 60°–75° C. by mixing with heat-stabilizing or pasteurization-stabilizing amounts of a polyol. Pasteurized compositions containing therapeutically active proteins heretofore unobtainable are available as a result of the process of our invention by heating a mixture of unpasteurized protein composition and a polyol suspended or solubilized usually in an aqueous medium at a temperature and for a time sufficient to pasteurize the protein composition. Significantly, the heat sensitive protein compositions can be pasteurized with a polyol as the sole heat-stabilizing agent. Following pasteurization or heat treatment, the polyol is removed totally or in part, as desired, from the protein composition by conventional techniques, and the pasteurized protein composition is processed according to conventional procedures for its ultimate therapeutic use.

The primary advantage of the invention is the availability of thermally stable and pasteurized therapeutically active protein compositions, which heretofore have been unknown and unattainable. Since the therapeutically active protein compositions of the invention can be heated with minimal loss of activity under conditions known to inactivate hepatitis virus, these valuable materials can be administered to patients, who can obtain the full therapeutic benefits thereof with a substantially reduced risk of being infected by the hepatitis virus.

Another advantage of the invention is that it may be applied to blood plasma prior to fractionation, to partially fractionated blood plasma, and to individual blood plasma fractions, as well as to individual blood plasma proteins themselves. Thus, the versatility of the present process can be seen. Pasteurization of blood plasma prior to fractionation allows fractionation techniques other than the Cohn process to be applied to whole plasma. In this fashion the yield of albumin can be increased by about 20% or more. To date the Cohn process has been relied upon to secure certain therapeutic fractions such as immune serum globulin which without pasteurization have a history of being non-hepatitis infective. It must be remembered that immune serum globulin has not been pasteurized prior to this invention.

DESCRIPTION OF THE PREFERRED EMBODIMENTS

As mentioned above, the products of the invention include pasteurized or heat-treated compositions comprising a thermally sensitive, therapeutically active protein capable of being stabilized during pasteurization or heating at temperatures of about 60°–75° C., preferably about 60°–70° C. when mixed with thermal-stabilizing or pasteurization-stabilizing amounts of a polyol, the pasteurized compositions containing or being free of polyol.

In the method of the invention, the protein composition to be pasteurized is suspended or dissolved in an aqueous medium with an amount of polyol sufficient to stabilize the protein composition during subsequent pasteurization. The concentration of polyol necessary to stabilize a protein composition in accordance with this invention depends on the type and concentration of therapeutically active protein in the protein composition and on the type of polyol itself. Generally, the thermal-stabilizing amount or pasteurization-stabilizing amount should be within the range of about 1–1000 parts, preferably 5–100 parts, of polyol per part of total protein in the protein composition. Generally, about one part of protein composition is mixed with about 1–500 parts, preferably 4–200 parts, of an aqueous medium containing about 10%, preferably about 30%, to saturation of polyol, on a weight to volume basis. The therapeutically active protein is considered to be stabilized if it retains a substantial portion, i.e., at least 50%, of its therapeutic activity during pasteurization. It is preferred that 70% or more of the therapeutic activity of the protein composition be retained during pasteurization. Consequently, the amount of polyol to be added should be such as to retain the above-recited amount of therapeutic activity.

After the protein composition has been mixed with the polyol, the mixture is heated at a temperature and for a time sufficient to pasteurize it. Thus, the mixture is pasteurized upon heating it under conditions known to inactivate hepatitis virus. Effective pasteurization to inactivate hepatitis virus and to substantially reduce the risk of hepatitis infection is obtained by heating an unpasteurized protein composition at a temperature of about 60°–75° C., preferably about 60°–70° C. for a period of about 10 hours, usually about 62°–65° C. for about 10 hours.

The pasteurization is carried out under pH conditions which approximate physiological conditions. Thus, the pH of the mixture usually should be within the range of about 5.5–8.0, preferably about 6.0–7.5. In general, physiological conditions are desirable, where possible, during pasteurization to insure the least disturbance to the therapeutically active protein composition.

The amount of a particular polyol required to stabilize a specific protein composition during pasteurization and the conditions necessary to pasteurize the composition can be determined readily by one skilled in the art using pilot trials in accordance with the teaching contained herein.

Following pasteurization the mixture of polyol and protein composition may be treated to remove all or part of the polyol. Conventional techniques can be employed to achieve this end. For example, the mixture can be dialyzed or diafiltered using an appropriate semipermeable membrane. Other means of removing the polyol will be suggested to those skilled in the art.

The pasteurized mixture may be treated to remove water therefrom by procedures well known in the art. For instance, the mixture can be freeze-dried or ultrafiltered and then freeze-dried. Furthermore, the mixture can be sterile-filtered by conventional methods prior to water removal.

The pasteurized protein compositions of the invention can be formulated into pharmaceutical preparations for therapeutic use. To prepare it for intravenous administration the protein composition is dissolved usually in water containing physiological substances such as sodium chloride, glycine, and the like and having a buffered pH compatible with physiological conditions. Generally, guidelines for intravenously administered protein compositions are established by governmental regulation.

Thermally sensitive, therapeutically active proteins included within the scope of the invention are those proteins generally administered to patients for preventative and/or curative purposes, which lose some therapeutic activity when heated above about 40°–45° C. and which are capable of being stabilized during pasteurization or heating at a temperature of about 60°–75° C. in the presence of a polyol. Examples of therapeutically active proteins that may be pasteurized in accordance with the present invention, by way of illustration and not limitation, are those proteins derived from venous blood plasma or placental plasma and include blood plasma, partially fractionated blood plasma, individual blood plasma fractions, and individual blood plasma proteins. Thus, for example, protein compositions pasteurizable by the method of the invention may include as the therapeutically active protein plasminogen, albumin, antihemophilic factor (Factor VIII), Plasma Protein Fraction (human), fibronectin (cold insoluble globulin), an immune serum globulin such as IgG, IgA, IgD, IgE, and IgM, high molecular weight kininogen (90,000–106,000), an immune globulin, intravenous (modified, either chemically or enzymatically or by fractional separation, immune serum globulin), FEIBA, antithrombin III, $\alpha$-1-antitrypsin, plasma proteins (molecular weight 1000–30,000) having growth activity, such as plasma growth hormone, somatomedin, prealbumin, plasminogen-streptokinase complex, ceruloplasmin, transferrin, haptoglobin, and prekallikrein, etc., and mixtures thereof. In addition, pasteurized compositions containing "defatted" albumin and "defatted" Plasma Protein Fraction (human), i.e., PPF (human), are available through the invention. The term "defatted" means that the albumin and PPF (human) contain no more fatty acid material than that present in the native state prior to pasteurization. The pasteurized defatted compositions can be administered to patients who cannot tolerate infusion of high fatty acid material such as that obtained using standard pasteurization stabilizing agents, namely, sodium caprylate and sodium acetyl-tryptophanate.

It is noteworthy that antihemophilic factor B (Factor IX) and prekallikrein activator cannot be pasteurized in the presence of a polyol in accordance with the above method. Indeed, these proteins lose substantially all their therapeutic activity under conditions under which the aforementioned protein compositions retain a substantial portion of their activity.

The term "polyol" means a substance with more than one hydroxyl group (—OH) and includes polyhydric alcohols and carbohydrates such as sugars. It is preferred that the polyol be water miscible, physiologically compatible with the protein, and have a low molecular weight, i.e., a molecular weight less than about 5000. Higher molecular weight polyols, e.g., polysaccharides such as dextrin, starch, glycogen, cellulose, pentosans, pectin, hemicellulose, and the like, are not preferred for use in the present method because they are generally water immiscible and are difficult to separate from the protein composition after pasteurization has been completed.

Typical examples of sugars that may be employed in our method are mono-, di-, and trisaccharides such as arabinose, glucose, galactose, fructose, ribose, mannose, rhamnose, sucrose, maltose, raffinose, melezitose, and so forth. Exemplary of polyhydric alcohols or reduced sugars, included within the purview of the invention are erythritol, ribitol, sylitol, sorbitol, mannitol, etc.

Also within the compass of the invention are mixtures of polyols and substances that produce a polyol in the presence of water or heat such as hydrates, actonides, or the like.

It has been found that the fibrinogen (Factor I) content of the protein composition to be pasteurized is an important factor. The fibrinogen content of the protein composition should be no greater than about 60%, based on the weight of total protein, or no greater than 0.6% based on the weight of solution. In a preferred embodiment the protein composition should contain no greater than 40% fibrinogen, based on the weight of total protein, or no greater than 0.4% fibrinogen based on the weight of solution. If the amount of fibrinogen in the composition to be pasteurized exceeds the above limits, the thermal stability imparted to the therapeutically active proteins by the polyol is substantially reduced or lost completely.

A protein composition having a fibrinogen content greater than 60% can be pasteurized in accordance with our method (1) if the concentration of fibrinogen in the solution is below 0.6%, preferably below 0.4% or (2) if a protein capable of being stabilized during pasteurization such as albumin and the like is first added to the protein composition to lower its fibrinogen content to less than 60%. The added protein generally should have the characteristic of being easily separable from the initial protein composition if necessary. It may be also that the added protein is compatible with the intended therapeutic use of the initial protein composition and, thus, need not be removed therefrom.

The method of the invention may be used also in conjunction with other methods for inactivating hepatitis virus such as pasteurizing protein compositions in the presence of other stabilizers such as amino acids or heating protein compositions in the presence of substances known to kill hepatitis virus.

As the amino acid one may employ lysine, arginine, leucine, iso-leucine, methionine, phenylalanine, threonine, tryptophan, valine, alanine, aspartic acid, cysteine, glutamic acid, glycine, histidine, proline, serine, tyrosine, and the like. Substances producing the aforesaid amino acids such as an amino acid salt and the like also may be used. It should be understood that amino acids in the absence of a polyol are not effective pasteurization-stabilizing agents for those protein compositions that have been unpasteurizable prior to this invention.

Important products of this invention include pasteurized aqueous mixtures of polyol and therapeutically active protein compositions. Also included within the scope of this invention are pasteurized compositions free of polyol but containing a therapeutically active protein and those pasteurized protein compositions being free of polyol and water. Pharmaceutical preparations containing therapeutic amounts of a protein composition pasteurized in accordance with the present invention are also contemplated. Particular products of the invention are pasteurized compositions containing therapeutically active proteins that have not been pasteurized prior to this invention. For example, the products of the invention include pasteurized compositions containing antihemophilic factor (Factor VIII), plasma growth hormone, FEIBA, fibronectin, α-1-antitrypsin, ceruloplasmin, an immune serum globulin, somatomedin, prealbumin, an immune globulin, intravenous, plasminogen-streptokinase complex, transferin, plasma, prekallikrein, or high molecular weight kininogen.

As mentioned above the pasteurized products of the invention may be incorporated into pharmaceutical preparations, which may be used for therapeutic purposes. However, the term "pharmaceutical preparation" is intended in a broader sense herein to include preparations containing a protein composition pasteurized in accordance with this invention used not only for therapeutic purposes, but also for reagent purposes as known in the art; for tissue culture wherein organisms such as viruses for the production of vaccines, interferon, and the like, are grown on plasma or on plasma fractions, e.g., Cohn Effluent II+III, Cohn Fraction IV, Cohn Fraction V, and so forth; etc.

For any of the above uses it is advantageous that the protein composition be free of infective hepatitis as provided in the instant invention. The pharmaceutical preparation intended for therapeutic use should contain a therapeutic amount of a pasteurized protein composition, i.e., that amount necessary for preventative or curative health measures. If the pharmaceutical preparation is to be employed as a reagent, then it should contain reagent amounts of pasteurized protein composition. Similarly, when used in tissue culture or a culture medium the pasteurized protein composition should contain an amount of protein composition sufficient to obtain the desired growth. It should be obvious that protein compositions pasteurized in accordance with this invention will not contain infective amounts of viruses and other organisms which are inactivated under the pasteurization conditions.

The invention described above is demonstrated further by the following illustrative examples.

EXAMPLE 1

Pasteurization of Antihemophilic Factor

A. Four vials of KOATE ® antihemophilic factor (Factor VIII produced by Cutter Laboratories, Inc., Berkeley, Calif.) were reconstituted in 10 ml. of water-for-injection (WFI) each (1.9 mg. of protein/ml). The vials were pooled and saturated with sucrose (0.8 g/ml). The mixture was heated at 60° C. for 10 hours to pasteurize it and then dialyzed overnight against final container AHF buffer (0.3 M glycine, 0.15 M sodium chloride, 0.01 M sodium citrate, and 1% dextrose).

As a control another vial of KOATE ® antihemophilic factor was reconstituted with 10 ml. WFI and saturated with sucrose. The sample was stored at 5° C. and was not heated at 60° C. for 10 hours. The stored sample was dialyzed as described in the preceding paragraph.

The pasteurized sample and the control from above were assayed as follows:

Total protein was determined by absorbancy measurements at 280 nanometers.

Procoagulant activity (VIII:C) was assayed by one stage Activated Partial Thromboplastin Time (APTT) test modified from the methods of Langdell et al., *J. Lab. Clin. Med.*, Vol. 41, pages 637–647 (1953) and Proctor et al., *Am. J. Clin. Path.*, Vol. 36, page 212 (1961).

Ristocetin-Willebrand factor activity (VIII R:WF) was assayed with gel-filtered platelets according to the method of Olson et al., *Am. J. Clin. Path.*, Vol. 63, pages 210–218 (1975).

Quantitative factor VIII antigen (VIII R:Ag) determinations were done according to the procedure of Laurell, *Anal. Biochem.*, Vol. 15, pages 45–52 (1966).

Antiserum against the Factor VIII related proteins was obtained from Behring Diagnostics (Sommerville, N.J.).

Protein species distribution was assayed by cellulose acetate electrophoresis.

The results are summarized in the table below.

TABLE 1

| Sample | VIII:C/ml (units) | $A_{280}$ (units) | Recovery of VIII:C (%)[a] |
|---|---|---|---|
| Pasteurized | 2.0 | 2.5 | 63[b] |
| Control | 3.1 | 3.6 | 66[b] |

TABLE 1-continued

| Sample | VIII:C/ml (units) | $A_{280}$ (units) | Recovery of VIII:C (%)[a] |
|---|---|---|---|
| Feed | 22.2 | 17 | — |

[a] $\frac{\text{units VIII:C/units } A_{280}}{\text{units VIII:C(feed)/units } A_{280} \text{ (feed)}} \times 100$

[b] These results indicate that the loss in AHF activity observed results from procedures other than the pasteurization step, such as the dialysis procedure.

B. AHF concentrate was prepared by a modified method of Hershgold et al., *J. Lab. and Clin. Med.*, Vol. 67, pages 23–32 (1966) from fresh frozen human plasma.

To an aqueous solution of AHF concentrate was added enough sodium citrate and sodium chloride to achieve concentrations of 0.01 M and 0.15 M, respectively, and glycine was added to a concentration of 1.6 M. The mixture was held at 5° C. for 1 hour. The precipitate that formed was collected by centrifugation and removed. The solution was dialyzed against 0.1 M glycine, 0.01 M citrate, and 0.15 M sodium chloride using an Amicon ® hollow fiber system (Amicon Corp., Bedford, Mass.) to reach final container levels of the above materials.

The AHF solution was concentrated by means of ultrafiltration using an Amicon PM10 membrane to an $A_{280}$ of 20. Following this step, the AHF solution was mixed with enough sucrose to yield a saturated sucrose solution (0.8 g/ml). The mixture was heated at 60° C. for 10 hours to pasteurize it and then dialyzed against final container AHF buffer.

The pasteurized AHF concentrate was analyzed according to the procedures enumerated in Part A of this Example. The results are tabularized in Table 2.

EXAMPLE 2

Pasteurization of Modified Immune Serum Globulin

Modified immune serum globulin (MISG) was prepared according to the method disclosed in U.S. Pat. No. 3,903,262 (herein incorporated by reference). The so-prepared MISG after diafiltration was saturated with sucrose by the addition of 0.8 g. sucrose per milliliter of MISG solution (66%). The mixture was heated at 60° C. for 10 hours to pasteurize it. The pasteurized material was diluted with an equal volume of WFI and diafiltered against WFI using a Romicon GM 80 diafilter (Romicon Corporation, Woburn, Mass.) for seven volume exchanges at room temperature and physiological pH of about 6.8±4.

After diafiltration, the MISG solution was formulated to give a 5% MISG aqueous solution containing 0.1 M glycine and 10% maltose and then was sterile-filtered.

As a control of unpasteurized 5% MISG aqueous solution containing 0.1 M glycine and 10% maltose was prepared from MISG as produced by the process of U.S. Pat. No. 3,903,262.

The pasteurized MISG solution and the control were assayed for anticomplement (AC) activity and measles, polio, and diphtheria potencies.

Also, SDS-PAGE patterns were compared for the pasteurized MISG solution and the control.

Anticomplement Activity: Anticomplement activity was measured by a standard dilution assay. Typically, 0.2 ml. of two-fold serial dilutions of the test substance was incubated for 2 hours at 37° C. with two "full" units of guinea pig complement in 0.4 ml. of saline. (One full unit of complement is that amount which causes complete hemolysis of 0.4 ml. of a 1 percent suspension of sensitized sheep erythrocytes). The residual complement was then determined by addition of 0.4 ml. of a 1% suspension of sensitized sheep erythrocytes and incubation for an additional 30 minutes at 37° C. The degree of hemolysis was estimated visually and the anticomplement titer was taken to be the greatest dilution of test substance which gave at least 50 percent hemolysis.

Antibody titers: Measles, polio type II and mumps antibodies were determined by tissue culture neutralization assays.

Varicella zoster antibodies were estimated by complement fixation.

Tetanus and diphtheria antibodies were evaluated by neutralization of the toxins in guinea pigs.

Antistreptolysin 0 was determined by hemolyses of sheep red blood cells.

Rabies antibodies were evaluated using the rapid fluorescent focus inhibition test (RFFIT).

Group B streptococcal activity was carried out using a guinea pig peritoneal phagocytic assay.

Anti A, Anti B were evaluated using the standardized Coomb's test.

Prekallikrein activator (PKA) and activatable F.XII were measured using a two stage N-α-benzoyl-L-arginine ethyl ester hydrochloride (BAEE) assay procedure.

Physical Tests: Gel permeation chromatography was carried out at room temperature using two 2.6×90 cm. columns in series containing Bio Gel ® A-1.5 m (Bi-oRad Laboratories, Richmond, Calif.).

SDS-PAGE (sodium dodecylsulfate-polyacrylamide gel-electrophoresis) was carried out using 5% gels. When SDS is added to a protein solution, it binds to the protein giving the complex a very large negative charge. In the process, all noncovalent interactions are disrupted. Resolution of the individual subgroups is then possible by taking advantage of the molecular sieving properties of polyacrylamide gels.

Ultracentrifuge (UC) analysis: UC analysis is carried out using the sedimentation velocity method. The sedimentation coefficient S, reported in Table 3, is a measure of the rate of sedimentation at 20° C. in water ($S_{20W}$) and is dependent on the weight and shape of the particle $$S \text{ value} = \frac{dx/d\kappa}{\omega^2 \chi}$$

$\chi$ = distance from center of rotation,
$\omega$ = angular velocity, radians/sec,

TABLE 2

| Sample | Vol. (l.) | $A_{280}$ | VIII:C (u/ml) | VIIIR:WF (u/ml) | VIIIR:Ag (u/ml) | $\frac{\text{VIIIR:Ag}}{\text{VIIIR:WF}}$ | Recovery VIII:C (%) | Recovery VIIIR:WF (%) |
|---|---|---|---|---|---|---|---|---|
| Pasteurized | 2.89 | 5 | 1.1 | 1.6 | 1.8 | 1.6 | 6 | 61 |
| Feed solution | 1.93 | 8.1 | 3.6 | 3.0 | 8.8 | 2.9 | 100 | 100 |

$\kappa$ = time, sec.

Pasteurized MISG meets all proposed requirements of the Bureau of Biologics of the Food and Drug Administration.

A 5% solution of unpasteurized starting MISG was heated at 60° C. in the absence of sucrose. The MISG gelled in 75 minutes. The results are summarized in Table 3.

Figure 1:
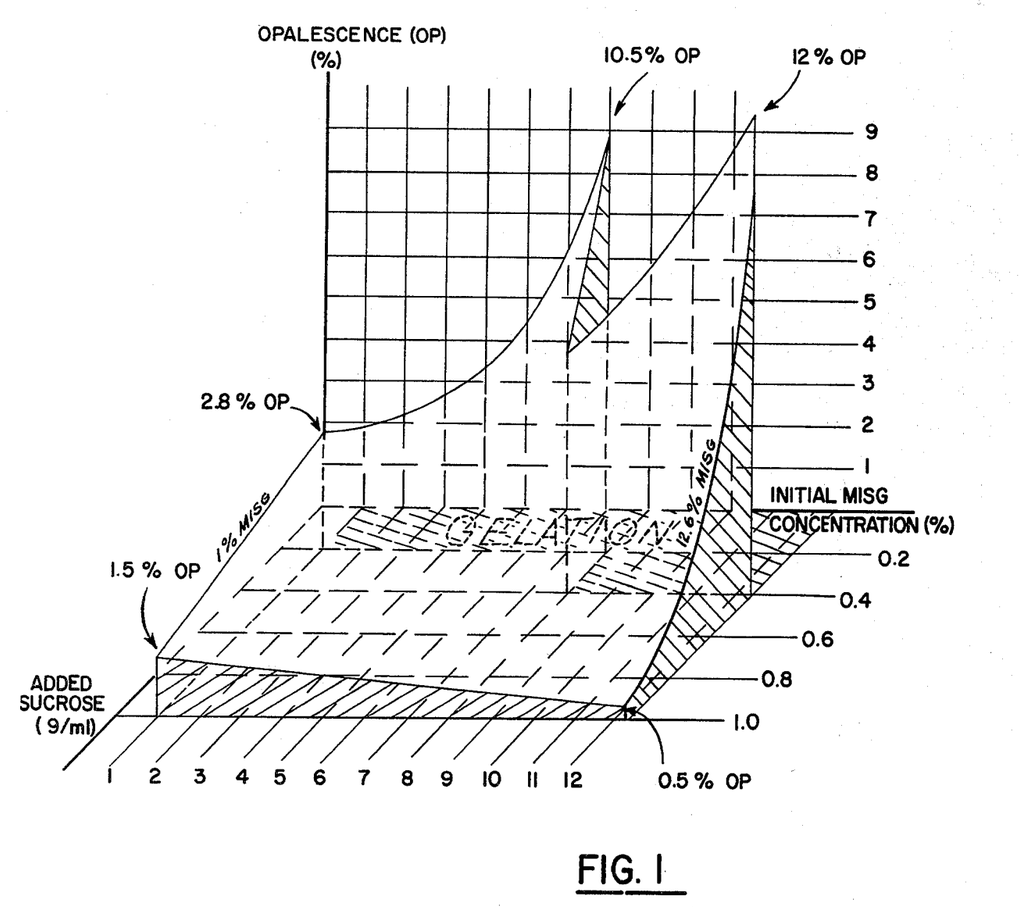
FIG. 1 is a three-dimensional view showing the relationship between sucrose concentration, concentration of modified immune serum globulin, and percent change in opalescence after pasteurization in the presence of sucrose.

It is apparent from FIG. 3 that the lower limit of sucrose concentration possible to secure pasteurization of a 5% solution of MISG is about 33%, which corresponds to the addition of 0.5 g. of sucrose per ml. of solution. Gelation occurs whenever added sucrose is less than 0.2 g./ml. Opalescence is indicative of degree of deactivation of MISG (U.S. Pat. No. 4,186,192).

TABLE 3

| ASSAY | CONTROL 5% MISG | PASTEURIZED 5% MISG |
|---|---|---|
| Antibody Screen: | | |
| Streptolysin 0, Todd units | 625 | 625 |
| Varicella Zoster | 1:64 | 1:64 |
| Measles | 0.5 | 0.3 |
| Polio, Type II | 0.2 | 0.3 |
| Diphtheria, units/ml | >1<2 | >1<2 |
| Tetanus, units/ml | 20 | 20 |
| Rabies, IU/ml | 64.6 | 53.8 |
| Anti A | 1:8 | 1:8 |
| Anti B | 1:4 | 1:4 |
| Group B Streptococcal Activity | ++ | ++ |
| Chemical: | | |
| Anticomplement Activity mg/C'H50 | 7.6 | 10 |
| PKA, mu/ml | 13.8 | 0 |
| Activatable F XII | 0 | 0 |
| Physical: | | |
| Gel Permeation Chrom. | | |
| % Void | 2.3 | 6.5 |
| % Dimer | 8.8 | 8.3 |
| % Monomer | 88.3 | 85 |
| % Monomer | 0.7 | 0.2 |
| SDS-PAGE | | |
| % Dimer (?) | 0 | 1.4 (?) |
| $H_2L_2$ | 3.2 | 3.3 |
| $H_2L$ | 4.5 | 3.4 |
| $H_2$ | 5 | 3 |
| HL | 8.1 | 7.4 |
| H | 52.5 | 53.7 |
| L | 26.6 | 27.8 |

| Ultracentrifuge | Initial +5° C. | 1 month 37° C. | Initial +5° C. | 1 month 37° C. |
|---|---|---|---|---|
| Material between 6.0–7.5 $S_{20}$ $w$ | 96 | 99 | 94 | 98 |
| Material between 7.6–12.0 $S_{20}$ $w$ | 4 | 1 | 6 | 2 |

EXAMPLE 3

Pasteurization of Plasminogen

Plasminogen was prepared as follows: Cohn Fraction III derived from human plasma ("The Proteins", Vol. II, 1954, pages 663–754, Academic Press, New York, N.Y.) was suspended in 0.1 M sodium phosphate, 0.15 M sodium chloride at pH 7.5. Plasminogen was isolated by a method similar to that disclosed by Deutsch et al., (Science, 1970, Vol. 170, pages 1095–1096) using lysine covalently coupled to a maleic anhydride tetraethylene glycol dimethacrylate copolymer instead of a lysine-Sepharose affinity medium. The so-prepared plasminogen (0.7 mg) was placed in a vial and reconstituted with 1 ml. of water for injection. The plasminogen solution was saturated with sucrose (0.8 mg/ml) and heated at 60° C. for 10 hours to pasteurize it. The yield of plasminogen was determined by first activating it to plasmin using streptokinase. The resulting plasmin was used to cleave standardized amounts of BAEE and the extent of cleavage was monitored spectrophotometrically at 255 nanometers (nm). The recovery of active plasminogen was 4 times as great as that for the control sample which was treated as follows:

0.7 mg. of so-prepared plasminogen was reconstituted in a vial by addition of 1 ml. of water for injection. The plasminogen solution was heated at 60° C. for 10 hours in the absence of sucrose. Analysis of the product was by the aforementioned technique.

EXAMPLE 4

Pasteurization of Plasma

Human blood plasma (300 ml.), obtained from donor plasma according to standard manufacturing techniques was saturated with sucrose (0.8 g/ml). The plasma-sucrose solution was heated at 60° C. for 10 hours to pasteurize it. No gelation was observed. The pasteurized plasma was diluted to twice its volume using 0.45% saline and was diafiltered against normal saline using an Amicon PM10 filter to remove added sucrose and then was concentrated by ultrafiltration to its original volume using the above filter.

As a control 10 ml. of human blood plasma from the same source as above was heated at 60° C. in the absence of sucrose.

The pasteurized plasma of the invention and unpasteurized starting plasma were analyzed by cellulose acetate electrophoresis (CAE). The results are outlined in the following table.

TABLE 4

| Sample | Albumin | Globulins | | | | |
|---|---|---|---|---|---|---|
| | | $\alpha_1$ | $\alpha_2$ | $\beta$ | $\phi$ | $\gamma$ |
| Pasteurized plasma | 61 | 2.7 | 8.5 | 10.7 | 6.9 | 10.2 |
| Starting plasma | 54.2 | 4.7 | 11.7 | 10.9 | 6.3 | 12.2 |
| Control | Gelled | | | | | |

It is noteworthy that no new peaks were seen by CAE analysis in the pasteurized plasma sample.

EXAMPLE 5

Pasteurization of Albumin

Dried Cohn Fraction V (greater than 96% albumin) powder (62.5 g) was suspended in 1.2 l. of 0.15 M saline. To this suspension was added 31.75 g of washed activated charcoal. The pH of the suspension was adjusted to 3.0 by addition of 6 N hydrochloric acid, and the suspension was stirred for 1 hour. Following centrifugation, the suspension was filtered through a Whatman No. 54 filter. The pH of the filtrate was adjusted to 7.04 by addition of 6 N sodium hydroxide and 10 ml of the solution was sterile filtered through a 0.2 micron filter.

The sterile filtered solution was saturated with sucrose (0.8 g/ml) and heated at 60° C. for 10 hours to pasteurize it. No gelation occurred during pasteurization. Sucrose was removed after pasteurization by dialysis against 0.9% saline.

SDS-PAGE analysis of the pasteurized albumin gave substantially the same results as those obtained for the unpasteurized starting albumin.

As a control a 5% solution of albumin was prepared as described in paragraph one of this example and heated at 60° C.; the solution was not saturated with sucrose prior to heating. The albumin gelled within the pasteurization period.

EXAMPLE 6

Pasteurization of Fibrinogen

One vial of Parenogen ® fibrinogen manufactured by Cutter Laboratories, Inc., was reconstituted in 100 ml. of water. The fibrinogen concentration in the reconstituted vial was 1000 mg/100 ml. as measured by Radial immunodiffusion (RID) using a M-Partigen ® fibrinogen plate (Behring Diagnostics, American Hoechst Corp., Somerville, N.J.). Aliquots of the fibrinogen solution were diluted in 0.07 M sodium citrate and pasteurized in 54% sucrose at 60° C. The results are summarized in Table 5.

TABLE 5

| Sample No. | Fibrinogen Concentration (mg/100 ml) | Observations |
|---|---|---|
| 1 | 1000 | Gelled in less than 20 min. |
| 2 | 800 | Gelled in less than 20 min. |
| 3 | 600 | Gelled in less than 20 min. |
| 4 | 400 | Slightly opalescent after 18 hrs. |
| 5 | 200 | Slightly opalescent after 18 hrs. |
| 6 | 100 | Clear after 18 hours |
| 7 | 50 | Clear after 18 hours |

These data show that fibrinogen is thermally stable at 60° C., 10 hours when present in concentrations less than 400–600 mg/100 ml. (0.4–0.6%). In the range of 400–600 mg/100 ml. the solutions became slightly opalescent indicating the onset of denaturation. Gelation results directly from protein denaturation (which is accompanied by substantial loss of activity).

EXAMPLE 7

Effect of Fibrinogen Concentration on Pasteurization of AHF

To four final container lots (A-D) of KOATE ® AHF and one in-process lot (E) was added enough sucrose to make the concentration therein about 54–56%. The fibrinogen content of each lot was determined by RID and cellulose acetate electrophoresis (CAE); the RID method gives the amount of fibrinogen in the solution whereas the CAE method gives the amount of fibrinogen in the protein composition. The lots were heated at 60° C. for 10 hours; the results are outlined in Table 6.

TABLE 6

| Lot | Fibrinogen by CAE (%) | Fibrinogen by RID (%) | Observations |
|---|---|---|---|
| A | 41 | 568 | No gelation |
| B | 35 | 194 | No gelation |
| C | 37 | 190 | No gelation |
| D | 62 | 477 | Gelation |
| E | 66 | 940 | Gelation |

EXAMPLE 8

DNA Polymerase Inactivation as a Measure of Reduction of Hepatitis

Introduction: The hepatitis B virus (HBV), the causal agent of serum hepatitis, has a diameter of 42 nanometers (nm) and is comprised of an outer surface coat and a 27 nm inner core. A unique DNA-dependent DNA polymerase is associated with the core of the virus. It is believed that this enzyme is responsible for endogenous DNA synthesizing activity. Kaplan et al., J. Virology, Vol. 12, pp. 995–1005 (1973) were able to confirm the presence of this enzyme in preparations rich in Dane particles. It was further shown that the peak enzyme activity seemed to correlate with the presence of Dane particles or cores when pellets of $HB_sAg$ were fractionated by sucrose density gradient ultracentrifugation. These Dane particles are usually found in very high concentrations during an acute infection with Hepatitis B virus. Bradley et al., Nature, Vol. 251, pp. 356–357 (1974) found DNA polymerase activity appearing in the serum of four of four chimpanzees after inoculation with HBV and before the appearance of $HB_sAg$ or clinical disease.

Although the infectivity of purified Dane particles has not been rigorously tested, it has been suggested by Robinson et al., New England J. Med., Vol. 295, pp. 1232–1236 (1976) that, if indeed the Dane particles represent the infectious form of the HBV, plasma infectivity might be expected to correlate better with DNA polymerase (DNAP) activity than with $HB_sAg$ values. Until infectivity of the Dane particle is proven conclusively, however, it must be recognized that DNAP activity could be manifested in an otherwise non-viable virus.

The assay used in this Example is a modification of the method developed by Robinson et al., supra. Four nucleotides, adenine triphosphate (ATP), cytosine triphosphate (CTP), guanosine triphosphate (GTP), and thymidine triphosphate (TTP) were employed in the DNA synthesizing procedure. Two of the nucleotides, dCTP and cGTP were radiolabelled with tritium. The DNA synthesizing action was allowed to proceed at 37° C. for 3 hours. Depending on the activity of the enzyme, variable amounts of radiolabel were incorporated into the DNA. After trichloroacetic acid precipitation and appropriate washing of the precipitate, the samples were counted in a scintillation counter.

Source of Hepatitis B virus: The virus was purified from $HB_sAg$ positive plasma by the following procedure. The above plasma was thawed and clarified by centrifugation at 6000 rpm, for 60 minutes at 40° C. The supernatant was then centrifuged at 50,000 xg for 16 hours at 4° C. to concentrate the virus. The resultant pellet was resuspended in 20% of the original plasma volume using 0.01 M Tris hydrochloric acid (Tris HCl), 0.001 M sodium ethylenediaminetetraacetate ($Na_2EDTA$) 0.1 M sodium chloride (NaCl), 0.1% (volume to volume) mercaptoethanol, and 0.1 mg/ml bovine serum albumin (BSA) and was clarified at 5000 rpm for 30 minutes at 4° C. to remove insoluble material.

Experimental: Approximately 0.1 ml. of virus preparation from above was added to 0.9 ml. of 5% albumin containing about 54% sucrose (0.8 g. of added sucrose/ml). The mixture was heated at 60° C. for 10 hours. Another sample prepared as above was heated at 64° C. for 10 hours.

Approximately 0.1 ml. of virus preparation from above was mixed with 0.9 ml. of 5% intravenous ISG containing about 54% sucrose, and the mixture was heated at 60° C. for 10 hours. The above was repeated at 64° C. for 10 hours using a similarly prepared intravenous ISG sample.

As a control 0.9 ml. of 5% albumin in 0.004 M sodium caprylate (SC) and 0.004 M acetyl-L-tryptophan (AT) was mixed with 0.1 ml. of the above-prepared virus, and the mixture was heated at 60° C. for 10 hours. Another 0.9-ml. sample of the above 5% albumin with stabilizers was mixed with 0.1 ml. of virus preparation and heated at 64° C. for 10 hours.

Heating the above controls at 60° C. and 64° C. for 10 hours was shown by Gellis et al., supra, to inactivate hepatitis virus to a non-infective level as shown by results obtained in the inoculation of human volunteers.

The term "substantially free of infective hepatitis" means free of active hepatitis virus to a non-infective level. The results are summarized in Table 7. (Tris hydrochloric acid=Tris (hydroxymethyl)aminomethanehydrochloric acid.

TABLE 7

| Sample | Pasteurization stabilizers | DNAP inactivation (%)[a] 64° C., 10 hrs | 60° C., 10 hrs |
|---|---|---|---|
| 5% albumin | 54% sucrose | 89 | 63 |
| 5% intravenous ISG | 54% sucrose | 96 | 92 |
| Control | 0.004M SC, 0.004M AT | 90 | 92 |

[a]Samples were assayed in duplicate.

The data show that heating at 64° C. for 10 hours produces approximately the same level of inactivation of DNAP in all samples and heating at 60° C. for 10 hours produces the same level of DNAP inactivation in the control and intravenous ISG samples. Consequently, since the level of DNAP inactivation in the samples pasteurized at 64° C. for 10 hours in accordance with the method of the invention is approximately the same as that in the control samples which are known to be non-hepatitis infective when pasteurized as above, it may be assumed that the samples of the invention are also non-hepatitis infective.

EXAMPLE 9

Pasteurization of Prekallikrein

Prekallikrein was prepared as follows: Human plasma was dialyzed against 0.05 M Tris, 0.2% Polybrene® solution at pH 8.0 to lower its ionic strength. The dialyzed plasma was then applied to a DEAE Sephadex-®A50 column and fractionated. The active prekallikrein peaks were pooled and then contacted with Concanavalin A-Sepharose ®. The Concanvalin A-Sepharose was washed, and prekallikrein was eluted with 0.5 M α-methylmannoside. The prekallikrein enriched solution (0.5 mg protein/ml) was dialyzed and sterile filtered. Fie milliliters of prekallikrein solution was mixed with sucrose (0.8 g/ml) and heated at 60° C. for 10 hours. The recovery of prekallikrein activity was determined by first activating it to kallikrein using excess prekallikrein activator (PKA or Factor XIIa). The resulting kallikrein was used to cleave standardized amounts of benzoyl arginine ethyl ester (BAEE). The extent of cleavage was monitored spectrophotometrically at 253 nanometers (nm). The recovery of prekallikrein activity was 85%.

As a control one ml. of prekallikrein solution without sucrose was heated at 60° C. Total activity was lost within three hours; no visual precipitation was observed.

EXAMPLE 10

Pasteurization of Fibronectin

Fibronectin was prepared by the method described by Engvall et al., Int. J. Cancer, Vol. 20, page 2 (1977) by the gelatin-Sepharose ® affinity medium method. Fibronectin was eluted from the affinity medium by washing with 4 M urea.

To remove urea the fibronectin-urea eluate was diafiltered using an Amicon ® hollow fiber membrane cartridge with a nominal retention of 10,000 molecular weight against Buffer A in 10% sucrose (0.1 g/ml).

The retentate was analyzed for fibronectin content by gel electrophoresis on unreduced and reduced sodium dodecylsulfate (SDS) polyacrylamide gel. The fibronectin band accounted for greater than 90% of the protein visible on the gel. The molecular weight of the fibronectin on unreduced SDS polyacrylamide gel was 400,000–500,000; the reported molecular weight is 450,000–500,000 by Yamade et al., Nature, 1978, Vol. 275, page 179. The molecular weight of the fibronectin on reduced SDS polyacrylamide gel was 250,000–270,000; the reported value is 210,000–250,000 by Yamade et al., supra.

The fibronectin was identified further by its amino acid composition, which agreed with that reported by Yamada et al., Biochemistry, 1977, Vol. 16, page 5552.

An antibody to the above-prepared purified fibronectin was prepared and it cross-reacted with commercially available fibronectin (Collaboration Research, Inc., Waltham, Mass.). In immunodiffusion studies the above-prepared fibronectin showed a line of identity with the commercial fibronectin when both samples were cross-reacted against the above antibody.

The above-prepared fibronectin was demonstrated to be greater than 95% pure as determined by stained SDS polyacrylamide gels.

Run A: The retentate (3.6 l.) was mixed with additional sucrose such that the final concentration of sucrose was 57% (0.57 g/ml.) The mixture was pasteurized by heating at 60° C. for 10 hours, was cooled, and was diafiltered against Buffer A (several volume exchanges) using an Amicon ® cartridge as described above to remove sucrose. Then, the solution was sterile filtered in Buffer A.

The activity of the pasteurized fibronectin (Run A) was determined by the following assays:

Rat Liver Slice Assay described by Molnar et al. in Biochemistry, Vol. 18, page 3909 (1979). The assay was performed in scintillation vials with 12 to 16 µg. of added fibronectin, 10 units of heparin, gelatin-coated latex particles labeled with $^{125}$I (10,000 cpm added to each vial), Krebs-Ringer buffer to a final volume of 1.2 ml., and a 100–150 mg. slice of fresh rat liver. This mixture was incubated for 30 minutes at 30°–37° C. with shaking. Uptake of labeled gelatin-latex, was enhanced up to 10 fold by native fibronectin and by sucrose-pasteurized fibronectin, but not by fibronectin which was heated at 60° C. for more than 30 minutes in the absence of sucrose.

Agglutination Assay described by Check et al. in the J. Reticuloendothelial Soc., Vol. 25, pages 351–362 (1979). The assay was performed in a manner similar to the liver slice assay. Fibronectin (2 to 31 µg, sometimes up to 600 µg) was added to vials containing 10 units of heparin, 300 µl. of a 0.6% solution of unlabeled gelatin-coated latex, and Krebs-Ringer buffer to a final volume of 1.2 ml. Vials were shaken for 30 minutes at 30°–37° C. Agglutination was scored visually by noting a transition from a milky solution to a clear solution with clumped particles. Activities are expressed as the lowest added amount of fibronectin at which agglutination occurs, and sucrose-pasteurized fibronectins caused visible agglutination of gelatin-latex particles at 8–23 μg of added fibronectin/vial. Fibronectin heated at 60° C. for more than 30 minutes in the absence of sucrose had to be added at levels more than 570 μg/vial to show agglutination, indicating a considerable loss of activity.

Run B: The experiment of Run A was repeated with the following addition: retentate after mixing with sucrose, was combined with arginine to a final concentration of arginine of 0.5 molar.

Run C: The experiment of Run B was repeated but no sucrose was added to retentate (not in accordance with the invention).

Run D: The experiment of Run C was repeated with 0.5 molar lysine in place of the arginine (not in accordance with the invention).

Run E: As a control retentate (3.6 l.) was heated at 60° C. for 10 hours, and was cooled, diafiltered and sterile filtered as described in Run A.

Run F: As a control retentate (3.6 l.) was constituted with sucrose to a concentration of 57% as in Run A and held at 5° C. for 10 hours. This sample was not heated.

Samples from Runs B-E were analyzed by the aforementioned assays. The results from Runs A-E are outlined in the following table.

TABLE 8

| Run | Pasteurization Conditions (60° C., 10 hours) | Recovery of therapeutic activity | |
|---|---|---|---|
| | | Agglutination assay (%) | Rat liver slice assay (%) |
| A | 57% sucrose | 105 | 120 |
| B | 57% sucrose, 0.5 M arginine | 118 | 60 |
| C[a] | 0.5M arginine | 10 | — |
| D[a] | 0.5M lysine | 5 | — |
| E[a] | control | <1 | 0 |
| F[a] | control, held at 5° C. for 10 hours | 100 | 100 |

[a]Not in accordance with the invention but provided for purposes of comparison.

The state of the pasteurized fibronectin was assessed by two additional assays:

Electrophoresis in non-denaturing buffers on polyacrylamide gels (Peacock, A. C., et al., Science 147, 1451, 1965). Samples of fibronectin were heated at 60° C. in Buffer A and examined by the above procedure. After 12 minutes at 60° C. pronounced changes were evident in the patterns on the stained gels, indicating aggregation and unfolding of the protein. In contrast, fibronectin pasteurized as above in 57% sucrose for 10 hours showed only a single band, as did unheated fibronectin. The relative mobility of both samples were the same. These results demonstrate that fibronectin does not aggregate or show other structural changes during pasteurization in sucrose.

Immunological Tests by the method of quantitative microcomplement fixation (Arnheim, et al., 1967, J. Biol. Chem., Vol. 242, p. 3951). For each sample of fibronectin a reaction curve with specific antiserum was determined. The reaction tubes contained 0.5 ml. of diluted antiserum, 0.5 ml. of antigen (3–1000 ng of fibronectin), and 0.5 ml of guinea pig complement. Antiserum to fibronectin was diluted 1:6000. Results of microcomplement fixation tests were expressed as a percent of the reactivity of unheated purified fibronectin.

Fibronectin pasteurized for 10 hours at 60° C. in 54% sucrose showed a 7–12% weaker reaction with antiserum than did unheated fibronectin. For this sensitive test such a variation in cross-reactivity is indicative of little or no change. For example, when unheated fibronectin was compared with human plasma (containing native fibronectin) a 17–30% change was noted. In other protein systems changes of this magnitude are observed between pairs of proteins which differ by single amino acid substitutions (Reichlin, J. Mol. Biol., Vol. 64, p. 485, 1972) or very slightly in conformation (Prager, et al., Immunochemistry, Vol. 3, p. 831, 1974). These results demonstrate that the structure of fibronectin essentially was unaltered by sucrose pasteurization.

EXAMPLE 11

Pasteurization of Effluent II+III

Effluent II+III was prepared by the alcohol fractionation method of Cohn (U.S. Pat. No. 2,390,074 and Journal of the American Chemical Society, supra). The effluent was stored at −80° C. until use.

A sample (930 g.) of Effluent II+III was diafiltered against 5.0 kg. of WFI and ultrafiltered until the retentate equalled 420 g., the pH (6.39) of the retentate was raised to 6.87 by addition of 4 N sodium hydroxide.

Sodium chloride 3.4 g. was added to 400 ml. of the diafiltered sample, which was then sterile filtered.

To 100 ml. of the so-prepared Effluent II+III was added 80 g. of sucrose. The mixture was heated at 60° C. for 16 hours to pasteurize it. The pasteurized sample was analyzed by CAE, which showed 4 peaks, albumin purity 79.6%. As a control CAE was applied to Effluent II+III that had not been heated; the analyses gave 4 peaks, albumin purity 83.9%. The results indicate that a substantial portion of the activity of the Effluent II+III was retained during the pasteurization process.

The pasteurized sample was dialyzed against 0.85% sodium chloride (1:400 v/v) and concentrated to an $A_{280}$ of 33.0 (the original $A_{280}$). The sample was sterile filtered and then frozen at −40° C.

Having thus described the invention, what is claimed is:

1. A method of pasteurizing a composition comprising a thermally sensitive, therapeutically active protein selected from the group consisting of antihemophilic factor (Factor VIII), fibronectin, plasminogen, antithrombin III, fibrinogen, alpha-1-antitrypsin, and prekallikrein, which comprises:
   (a) mixing the protein composition with a compound selected from the group consisting of sugars and reduced sugars in an aqueous medium said compound being present in the mixture in an amount of about 30% to saturation, on a weight to volume basis, and
   (b) heating the mixture at a temperature of about 60°–75° C. and a pH of about 5.5–8.0 for a time sufficient to pasteurize the protein composition and render it substantially free of infective hepatitis.

2. The method of claim 1 wherein the molecular weight of the compound is about 5000 or less.

3. The method of claim 1 wherein the mixture is heated in Step b at a temperature of about 62°–65° C.

4. The method of claim 1 wherein the mixture is heated for a period of about 10 hours.

5. The method of claim 1 which further includes the step of removing the compound from the mixture of Step b.

6. The method of claim 5 wherein the compound is removed from the mixture of Step b by subjecting the mixture to diafiltration or dialysis.

7. The method of claim 5 which further includes the step of removing water from the mixture of Step b.

8. The method of claim 7 wherein water is removed from the mixture of Step b by subjecting the mixture to ultrafiltration or freeze-drying.

9. The method of claim 1 wherein about 1–1000 parts of compound are mixed with 1 part of total protein.

10. A composition comprising a protein selected from the group consisting of antihemophilic factor (Factor VIII), fibronectin, fibrinogen, alpha-1-antitrypsin and prekallikrein produced by the method of claim 1.

11. A pharmaceutical preparation comprising a composition of claim 10.

12. A method of pasteurizing an antihemophilic factor concentrate, which comprises:
   (a) mixing the concentrate with a compound selected from the group consisting of sugars and reduced sugars in an aqueous medium, said compound being present in the mixture in an amount of about 30% to saturation, on a weight to volume basis and
   (b) heating the mixture at a temperature of about 60°–75° C. and a pH of about 5.5–8.0 for a time sufficient to pasteurize the antihemophilic factor concentrate and render it substantially free of infective hepatitis.

13. The method of claim 12 wherein about 1–1000 parts of compound are mixed with 1 part of total protein.

14. The method of claim 12 wherein about 1–500 parts of the aqueous solution are mixed with one part of concentrate.

15. The method of claim 12 wherein the mixture is heated in Step b at a temperature of about 62°–65° C.

16. The method of claim 12 wherein the mixture is heated for a period of about 10 hours.

17. The method of claim 12 which further includes the step of removing the compound from the mixture of Step b.

18. The method of claim 17 wherein the compound is removed from the mixture of Step b by subjecting the mixture to diafiltration or dialysis.

19. The method of claim 16 which further includes the step of removing water from the mixture of Step b.

20. The method of claim 19 wherein water is removed from the mixture of Step b by subjecting the mixture to ultrafiltration or freeze-drying.

21. A pasteurized antihemophilic factor concentrate produced by the method of claim 12.

22. A pharmaceutical preparation comprising the pasteurized antihemophilic factor concentrate of claim 21.

23. A method for pasteurizing a composition containing a thermally sensitive, therapeutically active protein selected from the group consisting of antihemophilic factor (Factor VIII), fibronectin, plasminogen, albumin, an immune serum globulin, a modified immune serum globulin, antithrombin III, Plasma Protein Fraction (human), fibrinogen, alpha-1-antitrypsin, human blood plasma, partially fractionated human blood plasma and prekallikrein, which comprises:
   (a) mixing the protein composition with an aqueous medium containing a heat stabilizing compound consisting essentially of non-heat treated sugars and reduced sugars, said compound being present in the mixture in an amount of about 30% to saturation, on a weight to volume basis and
   (b) heating the mixture at a temperature of about 60°–75° C. and a pH of about 5.5–8.0 for a time sufficient to pasteurize the protein composition and render it substantially free of infective hepatitis.

24. The method of claim 23 wherein about 1–500 parts of the aqueous medium are mixed with one part of protein composition.

25. The method of claim 23 wherein the mixture is heated in Step b at a temperature of about 62°–65° C. for a period of about 10 hours.

* * * * *